(12) United States Patent
Zou et al.

(10) Patent No.: US 7,701,561 B2
(45) Date of Patent: Apr. 20, 2010

(54) POLARIZATION IMAGING APPARATUS

(75) Inventors: Yingyin Kevin Zou, Lexington, MA (US); Qiushui Chen, Andover, MA (US); Hongzhi Zhao, Malden, MA (US)

(73) Assignee: Boston Applied Technologies Incorporated, Woburn, MA (US)

(*) Notice: Subject to any disclaimer, the term of this patent is extended or adjusted under 35 U.S.C. 154(b) by 507 days.

(21) Appl. No.: 11/701,738

(22) Filed: Feb. 2, 2007

(65) Prior Publication Data
US 2007/0296958 A1 Dec. 27, 2007

Related U.S. Application Data

(60) Provisional application No. 60/772,779, filed on Feb. 13, 2006.

(51) Int. Cl.
*G01N 21/00* (2006.01)
(52) U.S. Cl. .................................................. 356/73
(58) Field of Classification Search ............... 356/72, 356/73, 322
See application file for complete search history.

(56) References Cited

U.S. PATENT DOCUMENTS

| 5,412,500 | A | * | 5/1995 | Fergason ..................... 349/76 |
| 5,847,394 | A | | 12/1998 | Alfano et al. |
| 6,437,856 | B1 | | 8/2002 | Jacques |
| 6,700,694 | B2 | | 3/2004 | Zou et al. |
| 6,746,618 | B2 | | 6/2004 | Li et al. |
| 6,798,514 | B2 | | 9/2004 | Daniels |
| 6,816,261 | B2 | | 11/2004 | Patel et al. |
| 6,890,874 | B1 | | 5/2005 | Li et al. |
| 2003/0067667 | A1 | * | 4/2003 | Wang et al. ................. 359/323 |

OTHER PUBLICATIONS

S. Rahmann et al., "Reconstruction of specular surfaces using polarization imaging," IEEE Computer Society Conference on Computer Vision and Pattern Recognition, vol. 1, pp. 149-155, 2001.
S.G.Demos, et al., "Deep subsurface imaging in tissues using spectral and polarization filtering," Optics Express, vol. 7, No. 1, pp. 23-28, 2000.
H. Zhao, et al., "Polarization imaging sensor for cell and tissue imaging and diagnostics," Proc. of SPIE vol. 6380, pp. 638006-1~11, 2006.

* cited by examiner

*Primary Examiner*—Tarifur Chowdhury
*Assistant Examiner*—Abdullahi Nur

(57) ABSTRACT

A polarization imaging apparatus measures the Stokes image of a sample. The apparatus consists of an optical lens set 11, a linear polarizer 14 with its optical axis 18, a first variable phase retarder 12 with its optical axis 16 aligned 22.5° to axis 18, a second variable phase retarder 13 with its optical axis 17 aligned 45° to axis 18, a imaging sensor 15 for sensing the intensity images of the sample, a controller 101 and a computer 102. Two variable phase retarders 12 and 13 were controlled independently by a computer 102 through a controller unit 101 which generates a sequential of voltages to control the phase retardations of VPRs 12 and 13. A set of four intensity images, $I_0$, $I_1$, $I_2$ and $I_3$ of the sample were captured by imaging sensor 15 when the phase retardations of VPRs 12 and 13 were set at (0,0), ($\pi$,0), ($\pi$,$\pi$) and ($\pi/2$,$\pi$), respectively Then four Stokes components of a Stokes image, $S_0$, $S_1$, $S_2$ and $S_3$ were calculated using the four intensity images.

10 Claims, 5 Drawing Sheets

POLARIZATION IMAGING APPARATUS

CROSS REFERENCE TO RELATED APPLICATION

This application claims the benefit of Provisional Patent Application Ser. No. 60/772,779 filed Feb. 13, 2006.

STATEMENT OF GOVERNMENTAL INTEREST

This invention was made partially with Government supports under grant no NNJ05JC13C awarded by NASA. The government has certain rights in this invention.

BACKGROUND OF THE INVENTION

1. Technical Field

The invention relates to optical imaging apparatus, particularly related to polarization imaging apparatus, more specifically related to a high speed polarization imaging system that can measure Stokes components from a sample at different optical wavelengths.

2. Technical Background

The light scattered by a tissue has interacted with the ultrastructure of the tissue, which imprinted some intrinsic properties of the tissue. Tissue ultrastructure extends from membranes to membrane aggregates to collagen fibers to nuclei to cells. Photons are most strongly scattered by those structures whose size matches the photon wavelength. It has been demonstrated that light scattering can provide structural and functional information about the tissue. One important biomedical application of optical imaging and spectroscopy is noninvasive or minimally invasive detection of pre-cancerous and early cancerous changes in human epithelium, such as dysplasia or carcinoma in situ.

In recent years there has been an increasing interest in the propagation of polarized light in randomly scattering media. The investigation of backscattered light is of particular interest since most medical applications aimed at the in-vivo characterization of biological tissue rely on backscattered light. By recording the spatially dependent response of a medium to a polarized point source, one may obtain information about the scattering particles that are not accessible to mere intensity measurements. A diagnostic imaging modality based on near-infrared (NIR) radiation offers several potential advantages over existing radiological techniques. First, the radiation is non-ionizing, and therefore reasonable doses can be repeatedly employed without harm to the patient. Second, optical methods offer the potential to differentiate between soft tissues, due to their different absorption or scatter at NIR wavelengths that are indistinguishable using other modalities. And third, specific absorption by natural chromophores (such as oxy-haemoglobin) allows functional information to be obtained. NIR imaging research has focused on a variety of possible clinical applications.

The fact that the polarization state of the light contains useful information has been shown in many literatures, for example. Rahmann and Canterakis in "Reconstruction of specular surfaces using polarization imaging," *IEEE Computer Society Conference on Computer Vision and Pattern Recognition*, vol. 1, pp. 149-155, 2001, describe how the polarization state of light can be used for the reconstruction of specular surfaces to determine the shape of 3-D objects. They use the fact that light reflected by dielectrics and metals becomes partially linearly polarized and that the direction of polarization depends on the orientation of the reflecting surface. Demos and Alfano in "Deep subsurface imaging in tissues using spectral and polarization filtering," *Optics Express*, vol. 7, no. 1, pp. 23-28, 2000, demonstrate a technique based on polarization imaging that allows for optical imaging of the surface as well as structures beneath the surface.

There have been several polarization imaging schemes published. In U.S. Pat. No. 6,437,856, inventor Steven Louis Jacques, which issued Aug. 20, 2002, and U.S. Pat. No. 5,847,394, inventors Robert R. Alfano, et al., which issued Dec. 8, 1998, a set of measurements at different polarization orientations are taken to render a new image that is independent of the light reflected from the surface of a tissue sample and that is dependent of the light scattered from deep tissue layers. Especially, a linearly parallel polarized light is used for illumination and two images are acquired, one image selecting linearly parallel (Par) polarized light (i.e., parallel to the light source-tissue-camera plane) and one image selecting linearly perpendicular (Per) polarized light (i.e., perpendicular to the light source-tissue-camera plane). A new image is obtained by (Par−Per) or (Par−Per)/(Par+Per).

Many polarimetric sensing technologies have been developed to capture the Stokes polarization information. People use rotating retarder, rotating polarizer to obtain Stokes parameters from several successive frames of image. In these mechanically-rotation approaches, however, the exact spatial registration between various frames is difficult due to changes of viewing angle and the polarization properties during the period of between successive frames in most target detection applications.

In U.S. Pat. No. 6,798,514, inventor James Maurice Daniels, which issued Sep. 28, 2004, the light passes through two liquid crystal waveplates and a polarizing filter before falling on a light sensitive element device to measure intensity of light in four different polarizations. However, the same difficulty also applied to the approach using liquid crystal for electro-optic polarization modulation, which usually has response time in the order of 100 ms. Another drawback for the liquid crystal approach is that polarization-rotating liquid crystals are not commercially available in many important IR bands.

SUMMARY OF THE INVENTION

It is therefore the main objects of the invention to provide a polarization imaging apparatus which can consistently provide high speed and broadband Stokes images in real-time.

The first key feature of the polarization imaging apparatus is that it provides fast adjustable optical phase control through high speed electro-optical variable phase retarders made from transparent electro-optic ceramics.

The second key feature of the invention is that the polarization imaging apparatus can be worked at a wavelength from 400 nm to 7 μm, using electro-optic ceramics.

The third key feature of the invention is that a simplified time sequential control and measurement algorithm which provides a fast measurement and converts sequential intensity images to Stokes images.

A preferred embodiment of the polarization imaging apparatus is shown in FIG. 1, which consists of a polarization imaging sensing unit 100, an electronic driver 101 and a computer 102. The imaging sensing unit 100 consists of an optical lens set 11, a linear polarizer 14 with its optical axis 18, a first variable phase retarder (VPR) 12 with its optical axis 16 aligned 22.5° to axis 18, a second variable phase retarder 13 with its optical axis 17 aligned 45° to axis 18, and a imaging sensor 15 for sensing the intensity images of the sample. The imaging sensor 15 can be a focal plan array (FPA) detector, a CMOS or a CCD sensor. Two VPRs 12 and 13 were controlled independently by a computer 102 through a controller unit 101 which generates a sequential of voltages to control the phase retardations of VPRs 12 and 13. A set of four intensity images, $I_0$, $I_1$, $I_2$ and $I_3$ of the sample were captured by imaging sensor 15 when the phase retardations of VPRs 12 and 13 were set at (0,0), ($\pi$,0), ($\pi$,$\pi$) and ($\pi/2$,$\pi$), respectively Then four Stokes components of a Stokes image, $S_0$, $S_1$, $S_2$ and $S_3$ can be calculated by computer 102 using the following formula:

$$\begin{cases} S_0 = 0.5 \times (I_0 + I_1) \\ S_1 = 0.5 \times (I_0 - I_1) \\ S_2 = 0.5 \times (I_2 - S_0) \\ S_3 = 0.5 \times (I_3 - S_0) \end{cases} \quad (1)$$

In one aspect, the present invention includes the ferroelectric materials, such as PLZT, La modified PMN-PT, and La modified PZN-PT to form the electric voltage controlled ferro-electric variable phase retarder.

Referring to FIG. 5 is another preferred embodiment of the polarization imaging apparatus consists of an illumination unit 50, a polarization imaging sensing unit 500, a controller unit 101 and a computer 102. The said illumination unit and imaging sensing unit are aligned in a reflection configuration. In addition to a light source, the illuminator may consist of parts such as a collimator, a polarizer or polarization modulator, and a fixed wavelength filter or tunable wavelength filter. Tunable optical band-pass filter is used to produce desired wavelength for the imaging, from visible to infrared (IR). The illuminator can produce a linear or arbitrary polarized light beam.

The illumination unit 50, and a polarization imaging sensing unit 500 in FIG. 5 can be further aligned in a transmission configuration, as illustrated in FIG. 6.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description present embodiments of the invention, and are intended to provide an overview or framework for understanding the nature and character of the invention as it is claimed. The accompanying drawings are included to provide a further understanding of the invention, and are incorporated into and constitute a part of this specification. The drawings illustrate various embodiments of the invention and together with the description serve to explain the principles and operations of the invention.

DETAILED DESCRIPTION OF THE PREFERRED EMBODIMENT

It is to be understood that the invention is not limited in its application to the details of the particular arrangement shown since the invention is capable of other embodiments. Also, the terminology used herein is for the purpose of description and not of limitation.

Figure 1:
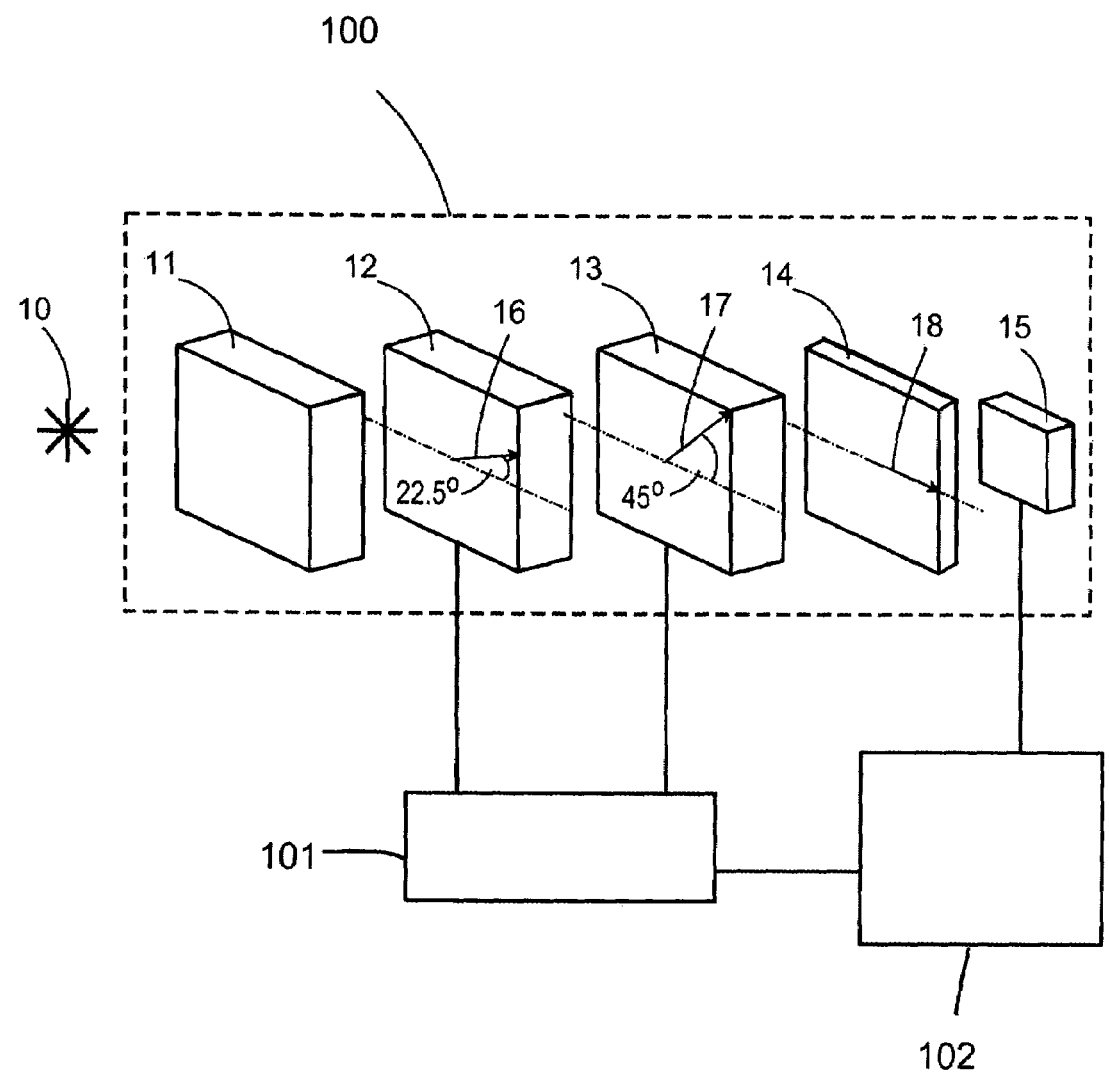
FIG. 1 is the schematic of a preferred embodiment of polarization imaging apparatus with variable retarders in accordance with the present invention.

FIG. 1 shows a preferred embodiment of the polarization imaging apparatus in accordance with the present invention. It consists of an imaging sensing unit 100, an electronic driver 101 and a computer 102. The imaging sensing unit 100 further consists of an optical lens set 11, a polarizer 14 with its optical axis 18, a first variable phase retarder (VPR) 12 with its optical axis 16 aligned 22.5° to axis 18, a second variable phase retarder 13 with its optical axis 17 aligned 45° to axis 18, a imaging sensor 15 for sensing the intensity images of the sample. The imaging sensor 15 can be a focal plan array (FPA) detector, a CMOS or a CCD sensor. The imaging sensing unit then is assembled inside a metal host (not shown). Two VPRs 12 and 13 were controlled independently by a computer 102 through a controller 101 which generates a sequential of voltages to control the phase retardations of the VPRs 12 and 13. The intensity images were captured through the imaging sensor 15, and processed by computer 102 to convert the sequential intensity images to Stokes images.

Using Mueller's calculus, we can obtain the Stokes parameters of an input light 10 by measuring the output light intensity of the sensor 15. The transformation done by the phase retarders can be described in the following equation, $$S_{out} = (S_{0,out} S_{1,out} S_{2,out} S_{3,out})^T = M_{r2} * M_{r1} * S_{in}. \quad (2)$$

where $S_{in} = (S_0\ S_1\ S_2\ S_3)^T$ is the unknown input Stokes vector of the target 10, which consists of four Stokes components. The parameter $S_0$ is the intensity of the light (including un-polarized component), $S_1$ is the intensity difference between horizontal linearly polarized and the vertical linearly polarized components, $S_2$ is the intensity difference between 45° linearly polarized and the 135° linearly polarized components, and $S_3$ is the difference between left- and right-circularly polarized intensities.

The quantities $M_{r1}$, and $M_{r2}$ are the Mueller matrices representing two variable phase retarders 12 and 13, respectively. These are given for the specific orientation by $$M_{r1}(\delta 1) = \begin{bmatrix} 1 & 0 & 0 & 0 \\ 0 & \frac{1}{2}(1+\cos(\delta 1)) & \frac{1}{2}(1-\cos(\delta 1)) & -\frac{1}{\sqrt{2}}\sin(\delta 1) \\ 0 & \frac{1}{2}(1-\cos(\delta 1)) & \frac{1}{2}(1+\cos(\delta 1)) & \frac{1}{\sqrt{2}}\sin(\delta 1) \\ 0 & \frac{1}{\sqrt{2}}\sin(\delta 1) & -\frac{1}{\sqrt{2}}\sin(\delta 1) & \cos(\delta 1) \end{bmatrix} \quad (3)$$

$$M_{r2}(\delta 2) = \frac{1}{2}\begin{bmatrix} 1 & 0 & 0 & 0 \\ 0 & \cos(\delta 2) & 0 & -\sin(\delta 2) \\ 0 & 0 & 1 & 0 \\ 0 & \sin(\delta 2) & 0 & \cos(\delta 2) \end{bmatrix} \quad (4)$$

where $\delta 1$ and $\delta 2$ are the two phase retardance introduced by the two variable phase retarders 12 and 13, respectively. To be able to measure the four components of the input Stokes vector, we need to set the variable phase retarders to at least four different states labeled as k. In the following, we detail the linkage between input state Stokes parameters and measured light intensity. The Mueller matrix for the cascaded variable retarders can be generally cast into an alternative form so that the state of polarization incident on the polarizer can be expressed as, $$\begin{pmatrix} S_{0,out} \\ S_{1,out} \\ S_{2,out} \\ S_{3,out} \end{pmatrix} = M \cdot \begin{pmatrix} S_{0,in} \\ S_{1,in} \\ S_{2,in} \\ S_{3,in} \end{pmatrix} = \begin{pmatrix} m_{00} & 0 & 0 & 0 \\ 0 & m_{11} & m_{12} & m_{13} \\ 0 & m_{21} & m_{22} & m_{23} \\ 0 & m_{31} & m_{32} & m_{33} \end{pmatrix} \cdot \begin{pmatrix} S_{0,in} \\ S_{1,in} \\ S_{2,in} \\ S_{3,in} \end{pmatrix} \quad (5)$$

The actually detected signal through the polarizer is essentially $$I = \frac{1}{2}(S_{0,out} + S_{1,out}).$$

Without worrying about a global factor, we throw away the factor of ½, thus the intensity can be expressed in terms of three of the Muller matrix elements, $$I = S_{0,out} + S_{1,out} = m_{00}S_{0,in} + m_{11}S_{1,in} + m_{12}S_{2,in} + m_{13}S_{3,in} \quad (6)$$

It is clear that the output intensity can be linked to the input Stokes parameters through generating four known states of polarization at the input so that we have, $$\begin{pmatrix} I_1 \\ I_2 \\ I_3 \\ I_4 \end{pmatrix} = A \cdot \begin{pmatrix} S_{0,in} \\ S_{1,in} \\ S_{2,in} \\ S_{3,in} \end{pmatrix} = \begin{pmatrix} m_{00}^1 & m_{11}^1 & m_{12}^1 & m_{13}^1 \\ m_{00}^2 & m_{11}^2 & m_{12}^2 & m_{13}^2 \\ m_{00}^3 & m_{11}^3 & m_{12}^3 & m_{13}^3 \\ m_{00}^4 & m_{11}^4 & m_{12}^4 & m_{13}^4 \end{pmatrix} \begin{pmatrix} S_{0,in} \\ S_{1,in} \\ S_{2,in} \\ S_{3,in} \end{pmatrix} \quad (7)$$

where $m_{ij}^k$ is the Mueller matrix element at the k-th state of variable retarders, and $I_i$ is the intensity measured with the i-th state of variable retarder. From Equation (7), it can be noticed that once the matrix A is known, the input Stokes parameters can be found out the inverse the matrix so that, $$\begin{pmatrix} S_{0,in} \\ S_{1,in} \\ S_{2,in} \\ S_{3,in} \end{pmatrix} = A^{-1} \cdot \begin{pmatrix} I_1 \\ I_2 \\ I_3 \\ I_4 \end{pmatrix} \quad (8)$$

The very question now is to find out the matrix A. It can be calculated from each Muller matrix in the system or, it can be done by generating four known states of polarization so that, $$A = \begin{pmatrix} S_{0,in}^1 & S_{0,in}^2 & S_{0,in}^3 & S_{0,in}^4 \\ S_{1,in}^1 & S_{1,in}^2 & S_{1,in}^3 & S_{1,in}^4 \\ S_{2,in}^1 & S_{2,in}^2 & S_{2,in}^3 & S_{2,in}^4 \\ S_{3,in}^1 & S_{3,in}^2 & S_{3,in}^3 & S_{3,in}^4 \end{pmatrix} \cdot \begin{pmatrix} I_1^1 & I_1^2 & I_1^3 & I_1^4 \\ I_2^1 & I_2^2 & I_2^3 & I_2^4 \\ I_3^1 & I_3^2 & I_3^3 & I_3^4 \\ I_4^1 & I_4^2 & I_4^3 & I_4^4 \end{pmatrix} \quad (9)$$

where $S_{i,in}^j$ is the i-th Stokes parameter generate by the j-th retardance. Thus we are able to link the input state polarization to the intensity measured at four retardance states. The Mueller matrix elements needed for finding the input state of polarization can be figured out through the use of four known state of polarization.

The measurement procedure is based on specifying above general principle for practical applications. As the configuration shown in FIG. 1, we can find out the useful Muller matrix elements (according to equation (6)) as follows:

$m_{00} = 1$ $m_{11} = \cos^2(\delta 1/2) \cdot \cos(\delta 2) - \sin(\delta 1) \cdot \sin(\delta 2)/\sqrt{2}$ $m_{12} = \sin^2(\delta 1/2)$ $m_{13} = -\cos^2(\delta 1/2) \cdot \sin(\delta 2) - \sin(\delta 1) \cdot \cos'(\delta 2)/\sqrt{2}$ \quad (10)

where $\delta 1$ and $\delta 2$ are the retardance of two VPRs 12 and 13, respectively. Although their values could be many different combinations for finding out the Stokes vector, the following 4-state procedure is considered to be the simplest yet most effective approach.

Figure 2:
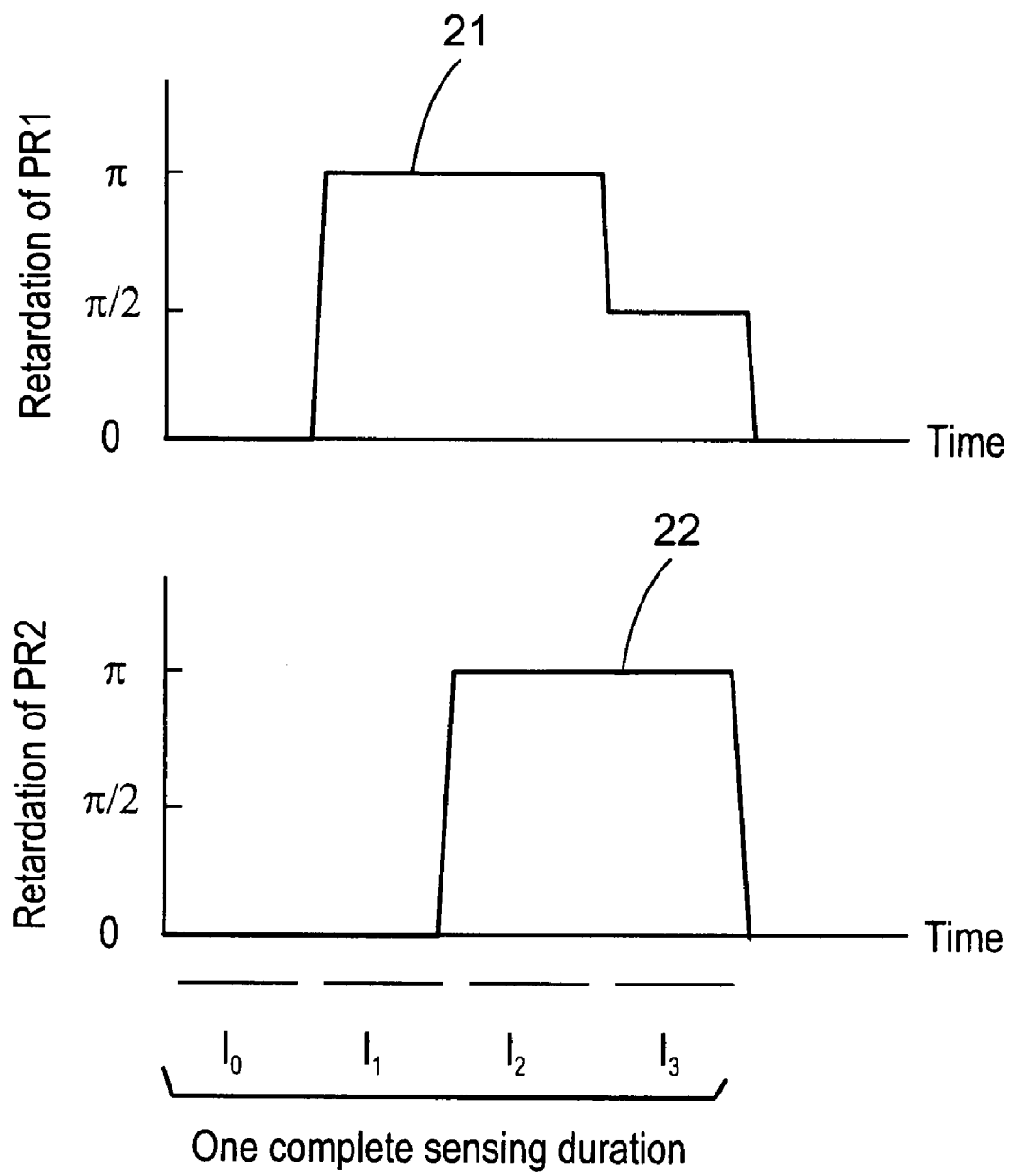
FIG. 2 shows the measurement steps for polarization imaging apparatus in accordance with the present invention.

Referring to FIG. 2 shows the procedure diagram to accomplish one measurement of Stokes parameters.

Four intensity images ($I_0$-$I_3$) are needed and taken sequentially, with two variable phase retarders 12 and 13 controlled by a sequence of voltages which were generated by controller 101. Phase retardation changes 21 and 22 of VPR 12 and VPR 13, respectively. $I_0$ is taken with 0 volt applied to both 12 and 13. $I_1$ is taken with the half-wave voltage $V_\pi$ applied to 12 and 0 volt applied to 13. $I_2$ is taken with $V_\pi$ is applied to both retarder 12 and 13. $I_3$ is taken with a quarter-wave voltage $V_{\pi/2}$ applied to 12 and $V_\pi$ applied to 13. The four Stokes vector images $S_0$-$S_3$ can be calculated from the intensity as follows:

$$\begin{cases} S_0 = 0.5 \times (I_0 + I_1) \\ S_1 = 0.5 \times (I_0 - I_1) \\ S_2 = 0.5 \times (I_2 - S_0) \\ S_3 = 0.5 \times (I_3 - S_0) \end{cases} \quad (11)$$

Table 1 listed the state of retardance of first and second variable phase retarders and the corresponding four intensities measured in each equal length time slot. The intensities also can be expressed as a function of Stokes parameters $S_0$-$S_3$ of the input Stokes vector according to equation (2). Table 1 also listed the formula for extracting the Stokes parameters $S_0$-$S_3$ from these intensities.

TABLE 1

| Time slot | 1 | 2 | 3 | 4 |
|---|---|---|---|---|
| State of VPR1 ($\delta 1$) | 0 | $\pi$ | $\pi$ | $\pi/2$ |
| State of VPR2 ($\delta 2$) | 0 | 0 | $\pi$ | $\pi$ |
| Measured intensity | $I_0$ | $I_1$ | $I_2$ | $I_3$ |

TABLE 1-continued

| Time slot | 1 | 2 | 3 | 4 |
|---|---|---|---|---|
| Relation to Stokes | $S_{0,in} + S_{1,in}$ | $S_{0,in} - S_{1,in}$ | $S_{0,in} + S_{2,in}$ | $S_{0,in} + S_{3,in}$ |
| Derived parameters | $\begin{cases} S_0 = 0.5 \times (I_0 + I_1) \\ S_1 = 0.5 \times (I_0 - I_1) \\ S_2 = 0.5 \times (I_2 - S_0) \\ S_3 = 0.5 \times (I_3 - S_0) \end{cases}$ | | | |

With this simple converting formula, Stokes images can be obtained using very simple calculation from the intensity images captured by an imaging sensor.

It should be pointed out that the switch of the relative positions of VPR 12 and VPR 13 will not affect the outcome of the Stokes images according to equation (2).

It is to be appreciated that the orientation configuration between the two variable phase plates 12 and 13 might be achieved with an intervening fixed waveplate, so that physical orientation of the two plates could be less constrained. Hence, the 22.5 degree orientation of the second variable phase retarder 13 with respect to the first variable phase retarder 12 of claim 1 is achieved by any combination of relative physical rotation of the second variable phase retarder 13 with respect to the first retarder 12 and rotation of the polarization reference frame between the two variable phase retarders 12 and 13 by a fixed phase retarding plate (not shown but included as part of the present invention).

Any other orientation configuration of first variable phase retarder 12 and second variable phase retarder 13 will also work, as long as the two variable retarders oriented at different angles, however may involve more difficult calculations.

In addition to the simplified measurement algorithm, a key component in this polarization imaging apparatus is the variable phase retarder. The other means to change the phase retardation, rotating waveplates, Faraday rotators and Pockel's cell have been used in laboratories worldwide. These devices, however, are bulky, high power consumption, slow or expensive.

A preferred variable phase retarder is made from an electro-optic (EO) material. The general requirement for an EO variable phase retarder is that, when a voltage is applied, a predetermined phase shift is produced for the light beam. Also the material is isotropic with no voltage applied, there is no residual birefringence to cause the initial phase shift. Preferably, the material has a high electro-optic coefficient in order to reduce operating voltages to less than 500 volts. Also the mechanical characteristics allow formation of a bar or plate for use as the electrode. Of course, the material must be transparent at the wavelength of interest, e.g., between 450 nm and 7 µm for most of the polarization imaging applications.

These requirements are satisfied by a class of ferroelectric complex oxides which 1) are optically isotropic; 2) have a Curie temperature less than about 490° C., so that electro-optic coefficients are high near room temperature; 3) have a diffusive phase transition, so that the temperature dependence of the electro-optic coefficients is lessened; and 4) which are not permanently poled by moderate electric fields since materials with a low Curie temperature that become permanently poled are less stable. Example material systems include electro-optic lanthanum modified PZT (PLZT), lead manganese niobate (PMN), a solid solution of lead zinc niobate and lead tantalate (PZN-PT), and a solid solution of lead manganese niobate and lead tantalate (PMN-PT). Besides PLZT, without being an exhaustive list the following materials and their solid solution with or without lanthanum modification, may be used: $Pb(Zr,Ti)O_3$, $Pb(Mg,Nb)O_3$, $PbTiO_3$, $Pb(Zn,Nb)O_3$ and $PbTaO_3$. These materials are available from Corning Inc. (Corning, N.Y.) and Boston Applied Technologies, Inc. (Woburn, Mass.), referenced as OptoCeramic® materials. These materials are electrical controllable, solid-state, high speed, low insertion loss, and low fabrication cost.

A preferred OptoCeramic® material, PMN-PT, for use in the present invention may be described by the general formula

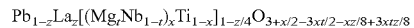

$$Pb_{1-z}La_z[(Mg_tNb_{1-t})_xTi_{1-x}]_{1-z/4}O_{3+x/2-3xt/2-xz/8+3xtz/8}$$

wherein x is between about 0.6 and about 0.95, z is between about 0 and about 0.08, and t is between about 0.30 and about 0.36. In especially preferred electro-optic ceramic materials of the present invention, z is between about 0.01 and about 0.06. In preferred electro-optic materials of the present invention, t may be between about 0.32 and about 0.34, and x may be between about 0.65 and about 0.90.

According to the present invention, the preferred OptoCeramic® PMN-PT is lanthanum modified solid solution of lead manganese niobate and lead tantalate (La:PMN-PT, or PLMNT) with a nominal 3.5/75/25 La/PMN/PT composition. For reference purposes nominal values for this PLMNT are n=2.48 and R=$11.5 \times 10^{-16}$ $m^2/V^2$ at 1.06 µm and n=2.458 and R=$6.86 \times 10^{-16}$ $m^2/V^2$ at 1.55 µm, both at 23° C. PLMNT has a polycrystalline structure with crystal sizes ranging from about 5 to 20 microns. In the form of hot-pressed ceramics, it is optically isotropic and exhibits little birefringence with zero applied voltage.

Figure 3:
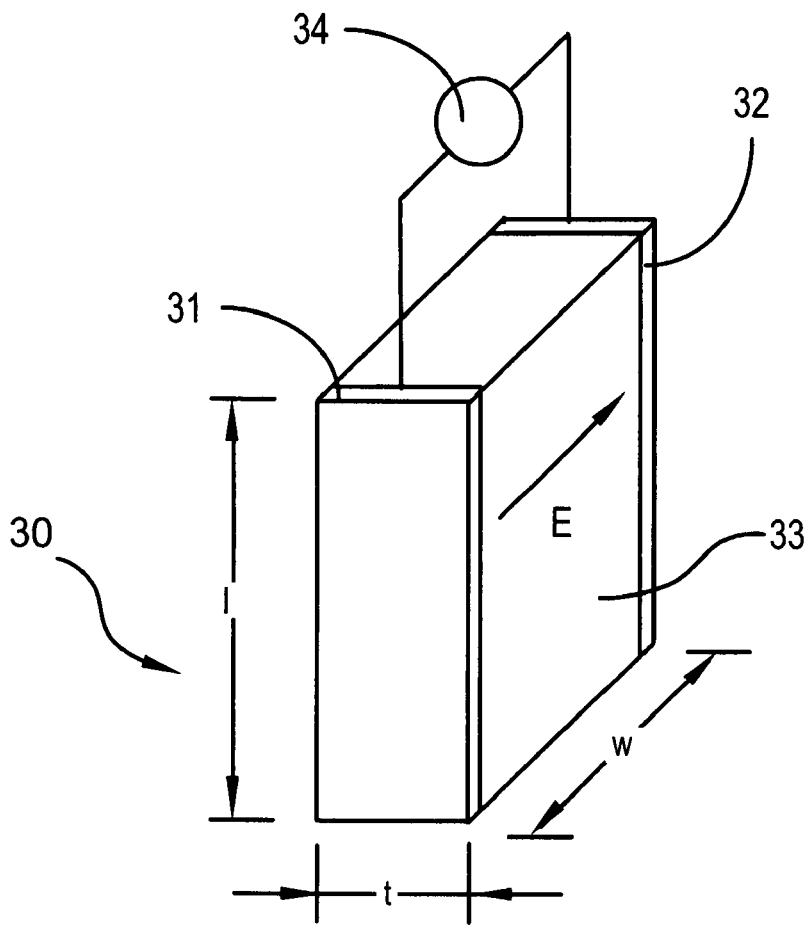
FIG. 3 shows the schematic drawing of a high speed variable retarder using a electro-optic ceramic.

An electrode geometry of phase retarder which takes advantage of these materials is illustrated by the transverse field configuration illustrated in FIG. 3. A plate 30, for use as the variable phase retarder 12 and 13 of FIG. 1, is shown which has thin metallized electrodes 31 and 32 on the both sides, respectively, of a block section 33 of EO material. The electrodes 31 and 32 are shown connected to a driving voltage 34 provide by controller 102 shown in FIG. 1. The electric field (designated E) is 90° to the direction of light propagation. Since the effect is based on the electric field in the material, it is desirable to arrange the electrodes as close together as possible to minimize the control voltage. The optical axis of the EO element is perpendicular to the electric field.

As an example, an EO phase retarder is made from a PLMNT plate with metallized electrodes, which has dimensions where the width (w) between the electrodes is about 5 mm, a thickness (t) of about 4 mm, and a length (l) of about 5 mm. Such a dimensioned PLMNT plate has an insertion loss of about 0.1 dB and half-wave voltage of 320V for a 700 nm wavelength laser at 23° C.

It will be understood that the particular geometry described is an example and that other device geometries can be used. Different dimensions of w and t can be selected to provide the same π phase shift with different control voltage. The other preferred PLMNT plate has dimensions of, but not limited to a width (w) of about 0.5-5 mm, a thickness (t) of about 1.30-5 mm, and a length (l) of about 1.0-5.0 mm.

Another preferred OptoCeramic® material is PLZT with a nominal 9.5/65/35 La/Pb/Zr composition. This composition is known to be transparent in a range from 450 nm to 7 µm; see, for example, Lionel M. Levinson, Electronic Ceramics, Chapter 7 (Marcel Dekker, New York, 1987).

Yet another preferred OptoCeramic® material, PZN-PT, for use in the present invention may be described by the general formula

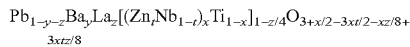

wherein x is between about 0.5 and about 0.9, y is between about 0.05 and about 0.5, z is between about 0 and about 0.05, and t is between about 0.30 and about 0.36. In especially preferred electro-optic ceramic materials of the present invention, x is between about 0.65 and about 0.85, y is between about 0.1 and about 0.2, z is between about 0.02 and 0.04, and t is between about 0.32 and about 0.34.

Figure 4:
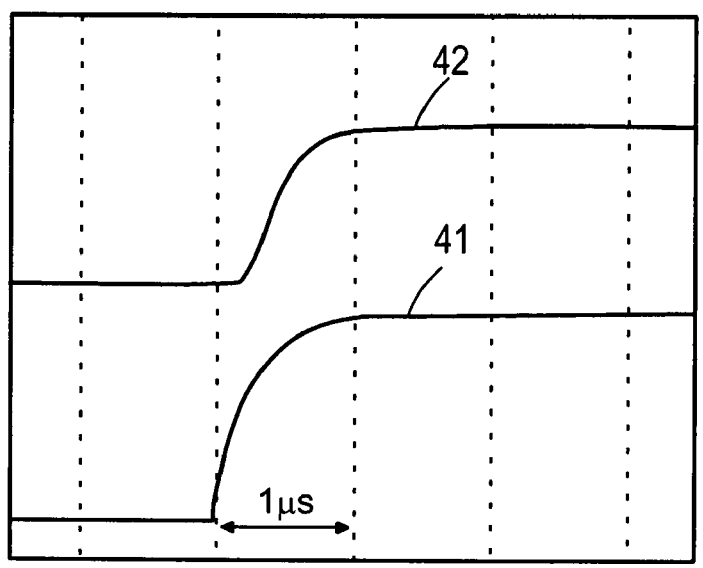
FIG. 4 shows measured responses of a high speed variable retarder.

Referring to FIG. 4 is the measured variable phase retarder response. The optical response 41 to the applied control voltage 42 is less than 1 microsecond. This means that the speed of setting and resetting of the VPR is as fast as 1.0 microsecond. According to the present invention, the imaging apparatus only needs 2 and 3 settings for the first and the second variable phase retarders 12 and 13 to complete a measurement cycle, respectively. The polarization sampling time could be less than 3 microseconds. This equals the system can generate a set of 4 Stokes component images at a speed of up to 300K frames per second (fps). With a fast enough imaging sensor, a real-time Stokes polarization imaging system can be realized.

In the present invention, another preferred EO material for variable phase retarders 12 and 13 are made from liquid crystals for a polarization imaging system working between the optical wavelengths 350 nm to 2000 nm. Using the invented control algorithm illustrated in FIG. 2, and relationship between sequential intensity images and Stokes images listed in Table 1, a fast polarization imaging system using LC variable retarders can also be configured.

Figure 5:
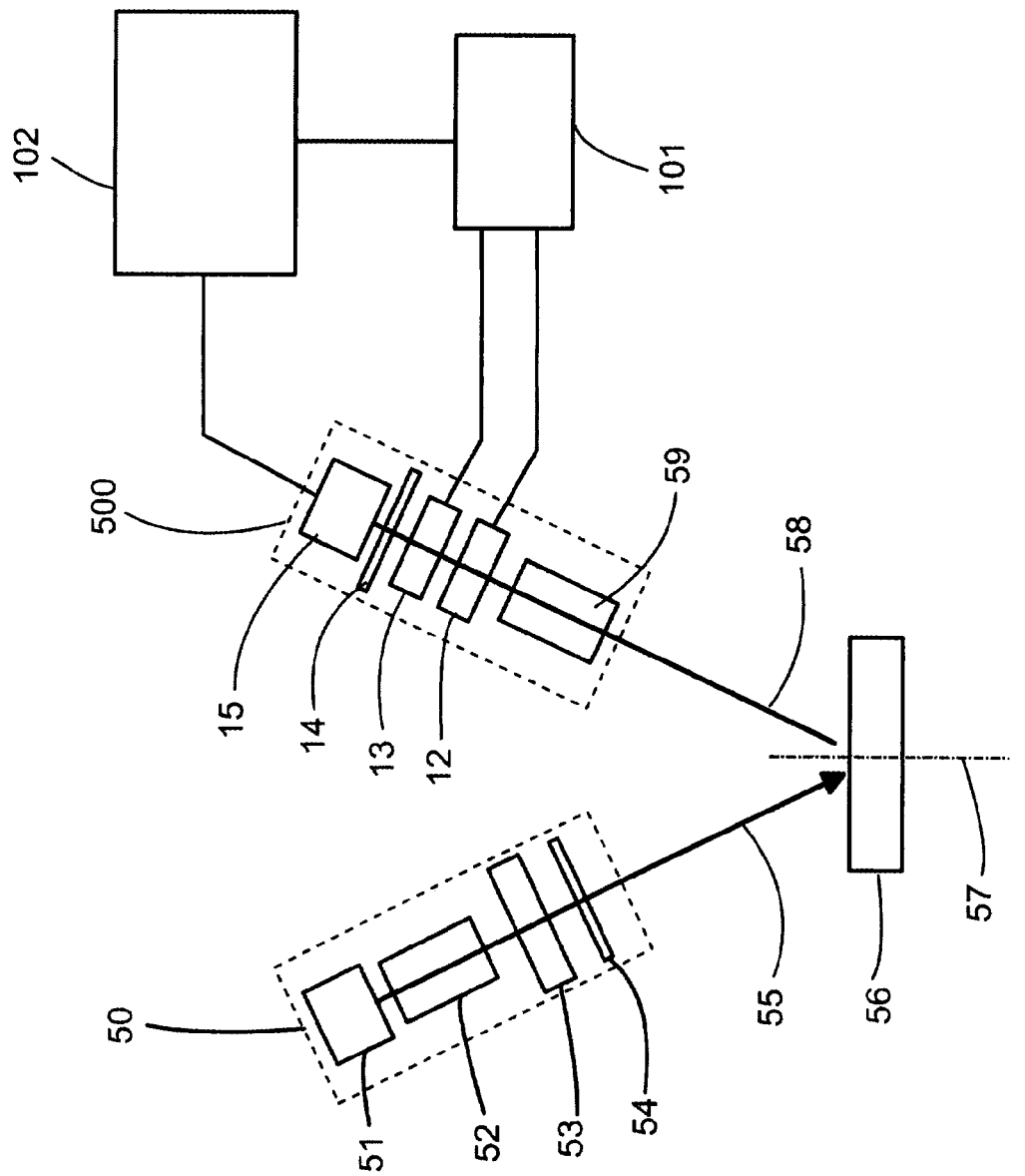
FIG. 5 is a schematic view of a preferred embodiment of reflective polarization imaging apparatus in accordance with the present invention.

A polarization imaging apparatus shown in FIG. 1 is basically a passive imaging system which using ambient light source to illuminate the sample. Referring to FIG. 5 is a schematic view of a preferred embodiment of an active polarization imaging apparatus in accordance with the present invention. It consists of an illumination unit 50 and an imaging sensing unit 500. The said illumination unit and imaging sensing unit are aligned in a reflection configuration. Both illumination unit 50 and imaging sensing unit 100 can be set to an angle related to sample 56 surface normal 57. In addition to a light source 51, the illuminator may consist of parts such as a collimator 52, a polarizer or polarization modulator 53, and a fixed wavelength filter or tunable wavelength filter 54. Tunable optical band-pass filter was used to produce desired wavelength for the imaging, from visible to infrared (IR). The illuminator could produce a linear or arbitrary polarized light beam.

A preferred light source 51 is a broadband light source, such as a tungsten-halogen lamp which provides a strong intensity over a broad spectrum from UV to NIR (300 nm to 2 μm). Another preferred light source is a light emitting diode (LED) source or laser source.

The scattering light 58 from sample 56 is detected by the imaging sensing unit 500. The optical lens set 11 in 100 shown in FIG. 1 can be an optical objective lens 59 in FIG. 5 with an infinite focal length, which makes the polarization imaging system a Stokes microscope.

The first VPR 12 and second VPR 13 were controlled independently by a computer 102 through a controller unit 101 which generates a sequential of voltages to control the phase retardations of VPRs 12 and 13. A set of four intensity images, $I_0$, $I_1$, $I_2$ and $I_3$ of the sample were captured by imaging sensor 15 when the phase retardations of VPRs 12 and 13 were set at (0,0), (π,0), (π,π) and (π/2,π), respectively Then four Stokes components of a Stokes image, $S_0$, $S_1$, $S_2$ and $S_3$ can be calculated by computer 102 according to equation (1).

Figure 6:
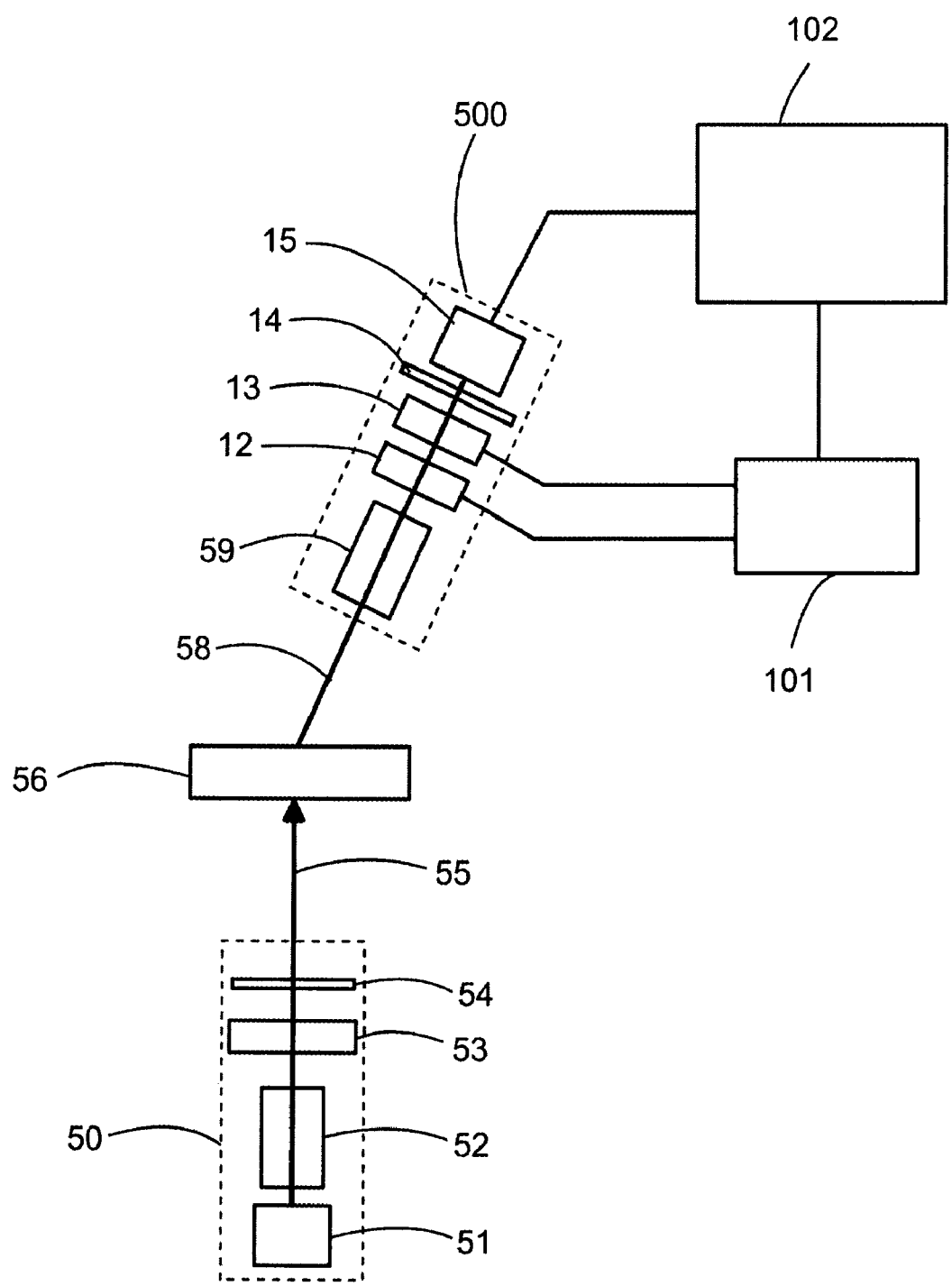
FIG. 6 is a schematic view of a preferred embodiment of transmissive polarization imaging apparatus in accordance with the present invention.

Referring to FIG. 6 is a schematic view of a polarization imaging apparatus shown in FIG. 5 configured in a transmission configuration.

It will be apparent to those skilled in the art that various modifications and variations can be made to the present invention without departing from the spirit and scope of the invention. Thus it is intended that the present invention cover the modifications and variations of this invention provided they come within the scope of the appended claims and their equivalents.

What is claimed is:

1. A polarization imaging apparatus for measuring Stokes images of a sample comprising:
   an optic lens set,
   a first variable phase retarder optically coupled to the optic lens set and oriented 22.5-degree angle with respect to the linear polarizer, the first variable phase retarder having a first controllable phase retardation;
   a second variable phase retarder optically coupled to the first variable phase retarder, the second variable phase retarder oriented at a 45-degree angle with respect to the linear polarizer, the second variable phase retarder having a second controllable phase retardation;
   a linear polarizer optically coupled to the second variable phase retarder;
   an imaging sensor optically coupled to the polarizer for sensing the intensity images of the sample through the linear polarizer;
   an controller for varying the first controllable phase retardation of the first variable phase retarder and for varying the second controllable phase retardation of the second variable phase retarders; and
   a computer for controlling the controller, recording a sequential of four intensity images by varying the first and second variable phase retarders and converting the four sequential intensity images to four components of a Stokes image.

2. The polarization imaging apparatus of claim 1 wherein the four components of a Stokes image are converted from four sequential intensity images when setting the first and second variable phase retarders at four different pair of phase retardations.

3. The four components of a Stokes image in claim 2 are converted from four sequential intensity images when setting the first and second variable phase retarders having the phase retardations of (0,0), (π,0), (π,π) and (π/2,π), using the formula:

$$\begin{cases} S_0 = 0.5 \times (I_0 + I_1) \\ S_1 = 0.5 \times (I_0 - I_1) \\ S_2 = 0.5 \times (I_2 - S_0) \\ S_3 = 0.5 \times (I_3 - S_0) \end{cases}$$

4. The polarization imaging apparatus of claim 1 wherein the four components of a Stokes image are converted from four sequential intensity images when setting the first and second solid-state ferroelectric variable phase retarders at four different pair of phase retardations.

5. The first and second solid-state ferroelectric variable phase retarders of claim 4 each comprises one of the materials in the lanthanum modified PMN-PT (PMN-PT) system, or lanthanum modified PZN-PT (PZN-PT) system.

6. The polarization imaging apparatus of claim 1 wherein the four components of a Stokes image are converted from four sequential intensity images when setting the first and second liquid crystal variable phase retarders at four different pair of phase retardations.

7. A method to measure Stokes images of a sample, the method comprising the steps of:
orienting a first variable phase retarder at a 22.5-degree angle with respect to the linear polarizer;
orienting a second variable phase retarder at a 45-degree angle with respect to the linear polarizer;
sensing a sequential of four intensity images with four sets of phase retardations while varying the first controllable phase retardation of the first variable phase retarder and varying the second controllable phase retardation of the second variable phase retarders; and
converting a sequential of four intensity images to four components of a Stokes image.

8. The method in claim 7, wherein the four sets of phase retardations of first and second variable phase retarders having the phase retardations of (0,0), (π,0), (π,π) and (π/2,π).

9. The method in claim 7, wherein the four components of a Stokes image are converted from four sequential intensity images when setting the first and second variable phase retarders having the phase retardations of (0,0), (π,0), (π,π) and (π/2,π), using the formula:

$$\begin{cases} S_0 = 0.5 \times (I_0 + I_1) \\ S_1 = 0.5 \times (I_0 - I_1) \\ S_2 = 0.5 \times (I_2 - I_0) \\ S_3 = 0.5 \times (I_3 - I_0) \end{cases}$$

10. The method in claim 7 further comprising the steps of:
illuminating the sample with a light source;
adjusting the light source polarization state; and
changing the light source wavelength spectrum.

* * * * *